United States Patent
Sanborn (10) Patent No.: US 9,957,244 B2
(45) Date of Patent: May 1, 2018

(54) CATALYST AND PROCESS FOR PRODUCING 2,5-FURANDICARBOXYLIC ACID FROM HYDROXYMETHYLFURFURAL IN WATER

(71) Applicant: ARCHER DANIELS MIDLAND COMPANY, Decatur, IL (US)

(72) Inventor: Alexandra Sanborn, Lincoln, IL (US)

(73) Assignee: Archer Daniels Midland Company, Decatur, IL (US)

(*) Notice: Subject to any disclaimer, the term of this patent is extended or adjusted under 35 U.S.C. 154(b) by 0 days. days.

(21) Appl. No.: 15/500,367

(22) PCT Filed: Aug. 5, 2015

(86) PCT No.: PCT/US2015/043710
§ 371 (c)(1),
(2) Date: Jan. 30, 2017

(87) PCT Pub. No.: WO2016/028488
PCT Pub. Date: Feb. 25, 2016

(65) Prior Publication Data
US 2017/0217917 A1    Aug. 3, 2017

Related U.S. Application Data

(60) Provisional application No. 62/038,923, filed on Aug. 19, 2014.

(51) Int. Cl.
*C07D 307/68* (2006.01)
*B01J 23/46* (2006.01)

(52) U.S. Cl.
CPC .......... *C07D 307/68* (2013.01); *B01J 23/462* (2013.01)

(58) Field of Classification Search
CPC ............................ C07D 307/68; C07D 307/48
USPC .................................................. 549/485, 488
See application file for complete search history.

(56) References Cited

U.S. PATENT DOCUMENTS

2014/0315262 A1* 10/2014 Sanborn et al. ..... C07D 307/46
549/488

OTHER PUBLICATIONS

Gorbanev, Y.Y. et al.: Effect of support in heterogeneous ruthenium catalysts used for the selective aerobic oxidation of HMF in water. Topics in Catalysis, vol. 54, pp. 1318-1324, 2011.*
Stahlberg, T. et al.: Aerobic oxidation of 5-(hydroxymethyl)furfuryl in ionic liquids with solid ruthenium hydroxide catalysts. Catalysis Letters, vol. 142, pp. 1089-1097, 2012.*

* cited by examiner

*Primary Examiner* — Charanjit Aulakh
(74) *Attorney, Agent, or Firm* — William B. Miller (57) ABSTRACT

A process is described for converting hydroxymethylfurfural to furanic products inclusive of 2,5-furandicarboxylic acid, comprising combining a quantity of hydroxymethylfurfural with water to provide an aqueous solution containing at least about five percent by weight of hydroxymethylfurfural, and combining the aqueous solution with an oxygen source in the presence of a heterogeneous ruthenium-based catalyst and under conditions which are effective for oxidizing hydroxymethylfurfural to furanic oxidation products inclusive of 2,5-furandicarboxylic acid, but in the substantial absence of any solvent for either hydroxymethylfurfural or 2,5-furandicarboxylic acid other than water.

8 Claims, 2 Drawing Sheets

CATALYST AND PROCESS FOR PRODUCING 2,5-FURANDICARBOXYLIC ACID FROM HYDROXYMETHYLFURFURAL IN WATER

This application is a national stage entry of International Application No. PCT/US2015/043710, filed Aug. 5, 2015, which itself claims the benefit of U.S. Provisional Patent Application No. 62/038,923, filed Aug. 19, 2014, each of the contents of which are incorporated by this reference.

TECHNICAL FIELD

The present invention relates to catalysts and related processes for producing 2,5-furandicarboxylic acid.

BACKGROUND ART

The use of natural products as starting materials for the manufacture of various large-scale chemical and fuel products which are presently made from petroleum- or fossil fuel-based starting materials, or for the manufacture of biobased equivalents or analogs thereto, has been an area of increasing importance.

Agricultural raw materials such as starch, cellulose, sucrose or inulin are inexpensive and renewable starting materials for the manufacture of hexoses, such as glucose and fructose. It has long been appreciated in turn that glucose and other hexoses, in particular fructose, may be converted into other useful materials, such as 2-hydroxymethyl-5-furfuraldehyde, also known as 5-hydroxymethylfurfural or simply hydroxymethylfurfural (HMF):

Hydroxymethylfurfural

The sheer abundance of biomass carbohydrates available provides a strong renewable resource base for the development of commodity chemical and fuel products based on HMF.

In view of this fact, and due to HMF's various functionalities, it has been proposed that the HMF thus obtainable from hexoses such as fructose and glucose, could be utilized to produce a wide range of products derived from renewable resources, such as polymers, solvents, surfactants, pharmaceuticals, and plant protection agents. HMF has in this regard been proposed, as either a starting material or intermediate, in the synthesis of a wide variety of compounds, such as furfuryl dialcohols, dialdehydes, esters, ethers, halides and carboxylic acids.

A number of the products discussed in the literature derive from the oxidation of HMF. Included are hydroxymethylfurancarboxylic acid (HmFCA), formylfurancarboxylic acid (FFCA), 2,5-furandicarboxylic acid (FDCA, also known as dehydromucic acid), and diformylfuran (DFF). Of these, FDCA has been discussed as a biobased, renewable substitute in the production of such multi-megaton polyester polymers as poly(ethylene terephthalate) or poly(butylene terephthalate). Derivatives such as FDCA can be made from 2,5-dihydroxymethylfuran and 2,5-bis(hydroxymethyl)tetrahydrofuran and used to make polyester polymers. FDCA esters have also recently been evaluated as replacements for phthalate plasticizers for PVC, see, e.g., WO 2011/023491A1 and WO 2011/023590A1, both assigned to Evonik Oxeno GmbH, as well as R. D. Sanderson et al., Journal of Appl. Pol. Sci. 1994, vol. 53, pp. 1785-1793.

While FDCA and its derivatives have attracted a great deal of recent commercial interest, with FDCA being identified, for instance, by the United States Department of Energy in a 2004 study as one of 12 priority chemicals for establishing the "green" chemical industry of the future, the potential of FDCA (due to its structural similarity to terephthalic acid) to be used in making polyesters has been recognized at least as early as 1946, see GB 621,971 to Drewitt et al, "Improvements in Polymer".

Unfortunately, while HMF and its oxidation-based derivatives such as FDCA have thus long been considered as promising biobased starting materials, intermediates and final products for a variety of applications, viable commercial-scale processes have proven elusive. Acid-based dehydration methods have long been known for making HMF, being used at least as of 1895 to prepare HMF from levulose (Dull, Chem. Ztg., 19, 216) and from sucrose (Kiermayer, Chem. Ztg., 19, 1003). However, these initial syntheses were not practical methods for producing HMF due to low conversion of the starting material to product. Inexpensive inorganic acids such as $H_2SO_4$, $H_3PO_4$, and HCl have been used, but these are used in solution and are difficult to recycle. In order to avoid the regeneration and disposal problems, solid sulfonic acid catalysts have also been used. The solid acid resins have not proven entirely successful as alternatives, however, because of the formation of deactivating humin polymers on the surface of the resins. Still other acid-catalyzed methods for forming HMF from hexose carbohydrates are described in Zhao et al., Science, Jun. 15, 2007, No. 316, pp. 1597-1600 and in Bicker et al., Green Chemistry, 2003, no. 5, pp. 280-284. In Zhao et al., hexoses are treated with a metal salt such as chromium (II) chloride in the presence of an ionic liquid, at 100 degrees Celsius for three hours to result in a 70% yield of HMF, whereas in Bicker et al., sugars are dehydrocyclized to HMF at nearly 70% reported selectivity by the action of sub- or supercritical acetone and a sulfuric acid catalyst.

In the acid-based dehydration methods, additional complications arise from the rehydration of HMF, which yields by-products such as, levulinic and formic acids. Another unwanted side reaction includes the polymerization of HMF and/or fructose resulting in humin polymers, which are solid waste products and act as catalyst poisons where solid acid resin catalysts are employed, as just mentioned.

In consideration of these difficulties and in further consideration of previous efforts toward a commercially viable process for making HMF, Sanborn et al. in US Published Patent Application 2009/0156841A1 (Sanborn et al) describe a method for producing "substantially pure" HMF by heating a carbohydrate starting material (preferably fructose) in a solvent in a column, continuously flowing the heated carbohydrate and solvent through a solid phase catalyst (preferably an acidic ion exchange resin) and using differences in the elution rates of HMF and the other constituents of the product mixture to recover a "substantially pure" HMF product, where "substantially pure" is described as meaning a purity of about 70% or greater, optionally about 80% or greater, or about 90% or greater. An alternative method for producing HMF esters performs the conversion in the presence of an organic acid, which can also serve as the solvent. Acetic acid is mentioned in particular as a solvent for fructose. The resulting acetylated HMF product is reported to be "more stable" than HMF, because upon heating HMF is described as decomposing and producing byproducts "that are not easily isolated or removed," page 4, paragraph 0048. Sanborn et al. then proceed to describe the oxidation of the acetylated HMF product to provide FDCA, using a Co/Mn/Br Mid-Century type catalyst as well-known for the liquid phase oxidation of p-xylene to yield terephthalic acid (the conventional petroleum feed-derived commodity chemical that FDCA has been proposed to replace, for producing polyesters).

Still other recent publications describe like efforts to convert HMF to FDCA by a Mid-Century type oxidation process, see, for example, WO 2011/043661 to Muñoz de Diego et al. and WO 2013/033058 to Zuo et al, the latter involving a spray oxidation process with a solubilized Co/Mn/Br Mid-Century catalyst with acetic acid as a solvent.

While Mid-Century type oxidation methods are familiar to those in the terephthalic acid and polyester businesses and seemingly match up well with methods of making HMF derivatives as disclosed by Sanborn et al. and in the WO'661 reference to Muñoz de Diego et al., nevertheless these processes share the common challenge and added expense associated with removing and recycling an additional solvent such as acetic acid.

In WO 2013/106136 to Sanborn et al. (hereinafter "WO'136", such application hereby being incorporated herein by reference), a process is described for making HMF from an aqueous hexose solution through an acid dehydration, without the necessity of proceeding with an added solvent and without the necessity of proceeding through a "more stable" HMF derivative in order to avoid the formation of humins and like materials that would be undesirable in the context of further oxidizing the HMF (or HMF derivative) to FDCA of a suitable purity for polymer applications. In the WO'136 application, more particularly, an aqueous hexose solution is rapidly heated from an ambient to a reaction temperature in the presence of an acid catalyst, with a limited per-pass conversion of the hexose sugars to HMF prior to separation of a fermentation-ready residual sugars product from the HMF product. By carrying out a rapid dehydration of the hexose sugars in this fashion, the overall exposure of the HMF that is formed to acidic, elevated temperature conditions is correspondingly limited. The residual sugars product can be recycled for conversion to additional HMF, can be fermented to produce various products or put to other uses as referenced in the WO'136 application.

In view of the WO'136 process, it would be advantageous if an effective catalyst and process were then available for oxidizing HMF in an aqueous HMF feed such as produced according to the WO'136 application (wherein acetic acid need not be used to produce an HMF ester derivative) to provide FDCA; omitting the acetic acid would enable the considerable expense of recovering and recycling the acetic acid to the dehydration step to be avoided. Unfortunately, however, the knowledge base for HMF oxidation using other than the familiar Mid-Century type catalysts is relatively more limited.

U.S. Pat. No. 8,193,382 to Lilga et al., for example, describes oxidizing HMF in an aqueous solution with air or oxygen using a heterogeneous supported platinum catalyst. The aqueous HMF starting material can be basic, neutral or acidic, though the "relatively low solubility" of HMF oxidation products such as FDCA in neutral and acidic water requires that "appropriate reactor designs" are utilized to accommodate solids formation or that the HMF concentration in the feed is limited to avoid generating FDCA concentrations over the solubility limit in a combination of acetic acid and water; in the alternative, it is said that "solids formation and feed concentration are typically not problematic" under "mildly basic conditions" generating a carboxylate salt of FDCA (col. 5, lines 1-13). Use of a strong base such as NaOH is however cautioned against, as possibly leading to "undesirable side reactions such as the Cannizzaro reaction" (col. 5, lines 13-15). The oxidation catalysts are prepared by a complex method which involves calcination, mixing with platinum (II) acetylacetonate, rotary evaporation, repeated calcination, and reduction under hydrogen to an activated product, and then passivation under a flow of 2% O2.

Casanova et al. "Biomass into Chemicals: Aerobic Oxidation of 5-Hydroxymethyl-2-furfural into 2,5-Furandicarboxylic Acid with Gold Nanoparticle Catalysts", ChemSusChem, vol. 2, issue 12, pp 1138-1144 (2009) describe heterogeneous, nanoparticulate gold catalysts on a ceria support for the aerobic oxidation of HMF to FDCA, wherein NaOH is used at an optimal NaOH/HMF ratio of 4:1 to desorb the acid product from the catalyst surface.

Zope et al., "Influence of Reaction Conditions on Diacid Formation During Au-Catalyzed Oxidation of Glycerol and hydroxymethylfurfural", Topics in Catalysis, vol. 55, pp 24-32 (2012) similarly evaluates the oxidation of an aqueous HMF solution in the presence of supported gold catalysts. An acknowledged "serious limitation" is that an added base is required, which increases the operating costs of the process and produces additional salt byproducts that have little value and may have a negative environmental impact (p. 25). Use of a highly basic catalyst support in place of the added inorganic base (NaOH) had been suggested by others, and while Zope et al. found that the product diacid (FDCA) was in fact formed with high selectivity, "extensive dissolution" of magnesium from the highly basic hydrotalcite support was also noted.

JP Patent Application Publication 2009-23916 differs somewhat in employing cupric bromide, 2,2'-bipyridine and (2,2,6,6,-tetramethylpiperidin-1-yl)oxyl (TEMPO) in an alkaline aqueous HMF solution to produce FDCA carboxylate salts by use of both the Cannizzaro reaction and oxidation. From 5.0 to 20 equivalents of alkali are indicated as most preferred for each molar equivalent of HMF, so that while the use of a precious metal catalyst is avoided, the process still does have the same "serious limitation" ascribed by Zope et al. to the processes using such precious metal catalysts.

Gorbanev et al., "Effect of Support in Heterogeneous Ruthenium Catalysts Used for the Selective Aerobic Oxidation of HMF in Water", Topics in Catalysis, vol. 54, pp 1318-1324 (2011) prescribe heterogeneous ruthenium-based catalysts for the aerobic oxidation of HMF in water, ostensibly without the added base described as a "serious limitation" by Zope et al., though on closer examination it is evident that the heterogeneous ruthenium-based catalysts require a basic support (so that the catalyst preparation method in 2.2 describes the addition of a base, except in the case of MgO—$La_2O_3$, which gives a basic reaction mixture without a prior base treatment); a control experiment performed without a basic support led to only 3% of FDCA and 2% of HMFCA with the rest being formic acid. Moreover, consistent with Zope's findings, evidence of dissolution of the basic supports was noted (p. 1321, second paragraph). As well, consistent with Lilga et al's teachings, Gorbanev et al. utilized a dilute HMF feed concentration (0.6 percent by weight) and undesirably high catalyst to substrate ratios for their Ru-based catalysts.

SUMMARY OF THE INVENTION

Accordingly, while the art does provide a few examples of catalytic methods for oxidizing HMF in an aqueous feed (such as may be produced using the fast dehydration method of the WO'136 application) to provide furanic oxidation products inclusive of FDCA, none provide a truly satisfactory solution for avoiding the added expense and other difficulties associated with the use of a solvent such as acetic acid.

The present invention, in one aspect, thus concerns a process for converting HMF to furanic products inclusive of FDCA, wherein a quantity of HMF is combined with water to provide an aqueous solution containing HMF in a concentration of at least about five percent by weight, and the aqueous solution containing HMF is combined with an oxygen source in the presence of a heterogeneous ruthenium-based catalyst and under conditions which are effective for oxidizing HMF to form furanic oxidation products inclusive of FDCA in the presence of the catalyst, but in the substantial absence of any solvent other than water.

In one embodiment, the catalyst has ruthenium as its sole active catalytic component.

In another embodiment, the catalyst is unsupported.

In yet another embodiment, the catalyst is an unsupported ruthenium oxide catalyst.

In one embodiment, the FDCA formed is hot-filtered away from the heterogeneous oxidation catalyst at a temperature sufficient to maintain the FDCA substantially entirely in an aqueous solution, and then precipitated from solution by cooling to recover a solid FDCA product.

In another embodiment, FDCA is separated from the catalyst by dissolution in a solvent which does not substantially solubilize the catalyst, for example, methanol, followed by filtration to recover the catalyst and by removal of the solvent to provide a high purity FDCA solid product.

In still another embodiment, the FDCA is derivatized in situ to provide a more water-soluble FDCA derivative (for example, a dimethyl ester of FDCA) that can then be filtered away from the solid catalyst for further use or further processed to recover the underivatized FDCA.

In a second aspect, the present invention relates to an integrated process for making FDCA from an aqueous hexose solution, wherein a process according to the incorporated earlier WO'136 application is used to produce an aqueous feed comprising one or more hexose dehydration products inclusive at least of HMF, and HMF in the aqueous feed is oxidized to produce FDCA using a catalyst and process according to the instant application.

In one embodiment according to this second aspect, a fast-dehydration process as described in the WO'136 application is first used to generate an aqueous HMF product and a residual sugars product, with the aqueous HMF product then being used to provide the aqueous feed for an oxidation process according to the present invention (in certain embodiments, this will require addition of dilution water to generate an aqueous feed for the oxidation having a desired concentration of HMF in water) and the residual sugars product being recycled to provide additional HMF, used to make other products by fermentation, or used in still other ways as previously described in the WO '136 application. Those skilled in the art will appreciate that, depending upon relative product demands, market pricing and other factors affecting the overall profitability of such an integrated process, the upstream fast-dehydration process for generating an aqueous HMF product can be operated in such a manner as to convert more or less of the hexose sugars to HMF as compared to the various other products that could be made from the hexose sugars, by means of further processing of the residual sugars portion of the overall product mixture.

Accordingly, in still another contemplated embodiment according to this second aspect wherein maximum production of HMF and of furanic oxidation products (such as but not being limited to FDCA, of course) therefrom is desirable, the fast-dehydration approach of the WO'136 application is used to generate an aqueous HMF product but with little to none of the residual sugars product portion being generated, and the aqueous HMF product is used for generating the aqueous HMF feed to the oxidation step of an integrated process.

Preferably, substantially no residual sugars remain for isolation or removal from overall product mixture, and the aqueous HMF product portion from the dehydration step is merely diluted by addition of dilution water to generate an aqueous HMF feed of a desired concentration that then undergoes an oxidation step.

Alternatively, the product mixture from the dehydration step is not used directly (except for dilution) to provide the aqueous HMF feed that is then oxidized, but only so much of a residual sugars product portion is produced in the dehydration step and removed from an overall dehydration products mixture as is necessary to avoid excessive deactivation of the ruthenium-based oxidation catalyst or other like difficulties in the subsequent oxidation step, as would otherwise be experienced with the amounts of humins and other degradation byproducts of hexose sugars dehydration that would be generated by aggressively carrying out the dehydration step to generate no residual sugars portion and produce an aqueous HMF product portion that can be used directly (except for dilution) in the subsequent oxidation step to produce furanic oxidation products inclusive of FDCA.

DESCRIPTION OF EMBODIMENTS

The present invention may be more completely understood by describing certain embodiments in greater detail. These embodiments are not to be taken as limiting the scope and breadth of the current invention as more particularly defined in the claims that follow, but are illustrative of the principles behind the invention and demonstrate various ways and options for how those principles can be applied in carrying out the invention.

For example, while the present application is concerned principally with a catalyst and process for the oxidation of HMF to provide furanic oxidation products inclusive of FDCA, those skilled in the art will appreciate that still other substrates can be contemplated for oxidation using the catalyst and process of the present invention to produce other desirable oxidation products in addition (or even in preference) to FDCA. Thus, for example, levulinic acid is (like HMF) a hexose dehydration product which can be oxidized by means of the inventive catalyst to provide succinic acid, which like FDCA has been identified as a promising biobased product alternative to conventional petroleum-derived commodities, for example, maleic anhydride, or as providing a biobased starting material for producing a chemical presently made from petroleum-derived feedstocks (for example, 1,4-butanediol, tetrahydrofuran and gamma butyrolactone).

Preferred substrates for oxidation are those which can be derived by dehydration from readily available carbohydrates from agricultural raw materials such as starch, cellulose, sucrose or inulin, especially fructose, glucose or a combination of fructose and glucose, though any such carbohydrate source can be used generally. Examples of suitable carbohydrate sources include, but are not limited to, hexose, fructose syrup, crystalline fructose, and process streams from the crystallization of fructose. Suitable mixed carbohydrate sources may comprise any industrially convenient carbohydrate source, such as corn syrup. Other mixed carbohydrate sources include, but are not limited to, hexoses, fructose syrup, crystalline fructose, high fructose corn syrup, crude fructose, purified fructose, high fructose corn syrup refinery intermediates and by-products, process streams from crystallizing fructose or glucose or xylose, and molasses, such as soy molasses resulting from production of soy protein concentrate, or a mixture thereof.

Most preferably, however, the substrates which are fed to the process in the aqueous feed for oxidation are those which are formed by an acid-catalyzed dehydration reaction from fructose, glucose or a combination of these, with 2-hydroxymethyl-5-furfuraldehyde (HMF) again being the sugars dehydration product that is principally of interest.

Figure 1:
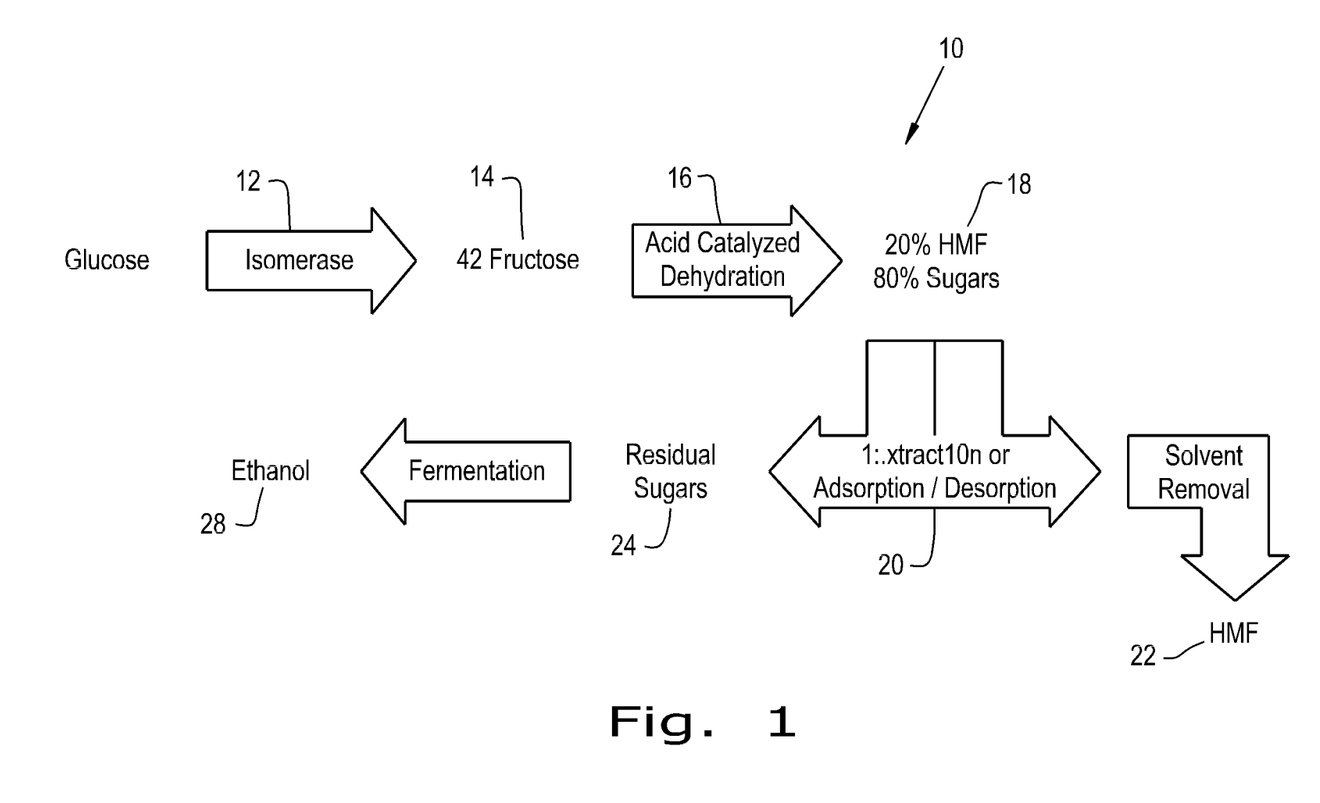
FIG. 1 corresponds to FIG. 1 of the WO'136 application, and provides a schematic representation of a process according to WO'136 in a preferred embodiment.

An embodiment 10 of a process according to WO'136 which may be used or adapted for use for providing an aqueous feed of HMF is shown schematically in FIG. 1 of the WO'136 application, which figure has been reproduced herein as FIG. 1 as well, though those skilled in the art will again appreciate that an aqueous solution of HMF in a concentration of at least five (5) percent by weight can be provided in a number of ways. For example, HMF may be combined with water by carrying out a dehydration of one or more hexose sugars in water, thus generating the HMF and additional water and in effect providing the desired aqueous HMF solution in the process of performing the dehydration. Equally, however, the HMF may be acquired rather than generated, and combined with a separate source of water in the appropriate proportions to provide an aqueous solution of HMF in a concentration of at least five percent by weight.

This having now been said, in the process embodiment 10, glucose as may be derived from the hydrolysis of starch with acids or enzymes or from the hydrolysis of cellulosic materials is first enzymatically converted in step 12 through use of an isomerase to a mixture of glucose and fructose, in the form of aqueous hexose sugar solution 14. Processes for making glucose from starch and for converting a portion of the glucose to fructose are well known, for example, in the making of high fructose corn syrups. Alternatively, of course, fructose derived from cane sugar or sugar beets, rather than from an isomerization of glucose, may be combined with glucose in a desired proportion. In still another embodiment, a combination of isomerization of glucose plus blending in of fructose from other known sources may be employed, to provide a combination of glucose and fructose for forming an aqueous hexose sugar solution for further processing. Preferably and conveniently, the aqueous hexose sugar solution 14 can correspond to a current high fructose corn syrup product, for example, HFCS 42 (containing 42 percent fructose and 53 percent glucose), HFCS 90 (made from HFCS 42 by additional purification, 90 percent fructose and 5 percent each of glucose and maltose) or HFCS 55 (containing 55 percent fructose, conventionally made from blending HFCS 42 and HFCS 90), so that existing HFCS production capacity can be utilized to make HMF and derivative products to improve asset utilization and improve returns on capital, as HFCS demand and pricing and HMF and HMF derivative demand and pricing would indicate.

The aqueous hexose sugar solution 14 then undergoes an acid-catalyzed dehydration in step 16. In the process of the WO'136 application, it is contemplated that some of the hexose sugars may not be converted but will remain in the product mixture 18 and would be of a character suited for direct use (if desired) by fermentation to produce ethanol. In this regard, in preferred embodiments of a dehydration process according to WO'136, the acid-catalyzed dehydration step 16 is conducted with rapid heating of the aqueous hexose sugar solution 14 from an ambient temperature to the desired dehydration reaction temperature, and then with rapid cooling of the HMF/unconverted sugar mixture 18 prior to the separation by a solvent extraction or adsorption/desorption step 20 of the fermentation-ready residual sugars product 24 from the HMF product 22. As well, the time from the introduction of sugar solution 14 until HMF/unconverted sugar mixture begins to be cooled is preferably also limited.

By accepting limited per-pass conversion to HMF and by conducting the acid-catalyzed dehydration as described, the overall exposure of the HMF that is formed to acidic, elevated temperature conditions may be correspondingly limited, so that it is possible to produce little to no humins or other like waste materials. Separation and recovery of the desired products is thereby simplified and levels of HMF and other hexose dehydration products known to inhibit ethanol production by fermentation may be reduced in the residual sugars product to an extent whereby the residual sugars product can be used directly for ethanol fermentation if desired (though a number of other uses of the residual sugars product are foreseeable, examples of which are subsequently cited).

Those skilled in the art will appreciate, however, in the context of the present invention—and in the particular context of an integrated process according to a second aspect summarized above—that it may be preferable at times to produce as little of the residual sugars product 24 as possible in carrying out an acid-catalyzed dehydration 16 of an aqueous hexose sugar solution 14 and maximize production of the HMF product 22 for subsequent oxidation according to the present invention. Where little to no residual sugars are produced, it may be possible in such circumstances to omit the separation step 20 and use the product mixture 18 for providing (or constituting itself) the aqueous HMF feed to a subsequent oxidation step. The degree to which the product mixture 18 can directly be used in this manner will depend in part on the effect on the subsequent oxidation catalyst of the amount of humins and other like byproducts that would be generated in the acid-catalyzed dehydration step 16, under the aggressive conditions that would be employed for maximizing HMF yield in the product mixture 18, as well as on other factors such as the value of the furanic oxidation products that can be made from the additional HMF compared to the value of the fermentation or other products that could have been made from the foregone residual sugars product 24, and the expenses associated with the separations step 20 and with further processing of a residual sugars product 24. In any event, those skilled in the art will be well able to determine the benefits and tradeoffs associated with producing certain proportions of the residual sugars product 24 as against the HMF product 22 in the context of an integrated process of the present invention, wherein a fast dehydration process otherwise according to the WO'136 application (but perhaps omitting entirely any production of residual sugars) is used to generate HMF for use in (or as) an aqueous feed to a ruthenium-based oxidation process according to the present invention.

Now in regard to the dehydration step 16, it will be appreciated that a variety of acid catalysts have been described previously for the dehydration of hexose-containing materials to HMF, including both homogeneous and heterogeneous, solid acid catalysts. Among the homogeneous catalysts, sulfuric acid was used in the examples of the WO'136 application, and provided good yields and excellent sugar accountabilities. A convenient alternative heterogeneous catalyst for the dehydration step 16 can be found in the same unsupported ruthenium oxide catalyst as preferred for use in carrying out the subsequent oxidation step of the HMF in or from the mixture 18, as demonstrated by an example below.

While we have observed some differences in the performance of the oxidation catalyst of the present invention as a function of pH at a given oxidation reaction temperature (as further explained below), nevertheless it is considered that those skilled in the art will be well able in view of the extensive art pertaining to the acid-catalyzed dehydration of hexoses and in view of the present application's teachings to select an appropriate catalyst for the dehydration step 16 in the context of an integrated dehydration/oxidation process according to the schematic embodiment of FIG. 3.

Returning now to FIG. 1, as previously indicated, where there remains unconverted, residual sugars in mixture 18 from the acid-catalyzed dehydration step 16, these may be separated from the HMF in the mixture 18 by adsorption, solvent extraction, or a combination of these in separation step 20, to yield an HMF product stream or portion 22 and a fermentation-ready sugars stream or portion 24, which stream or portion 24 can be recycled to produce additional HMF, or supplied to an ethanol fermentation step 26 for producing an ethanol product 28 (as shown) or put to other productive uses mentioned in the WO'136 application.

Adsorption in step 20 can be by means of any material which preferentially adsorbs HMF from the residual hexose sugars in the mixture 18. A material which has been found to be very effective at retaining the HMF and the small amounts of levulinic acid formed is DOWEX® OPTI-PORE® V-493 macroporous styrene-divinylbenzene resin (CAS 69011-14-9, The Dow Chemical Company, Midland, Mich.), which has been described by its manufacturer as having a 20-50 mesh particle size, a 46 angstrom mean pore size and 1.16 mL/g pore volume, a surface area of 1100 sq. meters/g and a bulk density of 680 g/liter. An ethanol wash was effective for desorbing most of the adsorbed HMF, and subsequent washing of the resin with acetone provided quantitative recovery of the HMF that was adsorbed. An alternative is AMBERLITE™ XAD™-4 polystyrene divinylbenzene polymeric adsorbent resin (CAS 37380-42-0, Rohm & Haas Company, Philadelphia, Pa.), a non-functionalized resin having a 1.08 g/mL dry density, a surface area of 725 square meters per gram, an average pore diameter of 50 angstroms, a wet mesh size of 20-60 and a pore volume of 0.98 mL/gram. Other suitable adsorbents can be activated carbon, zeolites, alumina, clays, non-functionalized resins (LEWATIT® AF-5, LEWATIT® S7968, LEWATIT® VPOC1064 resins, all from Lanxess AG), Amberlite® XAD-4 macroreticular crosslinked polystryrene divinylbenzene polymer resin (CAS 37380-42-0, Rohm & Haas Company, Philadelphia, Pa.), and cation exchange resins, see U.S. Pat. No. 7,317,116 B2 (Sanborn) and the later U.S. Pat. No. 7,897,794 (Geier and Soper). Desorption solvents may include polar organic solvents, for example, alcohols such as ethanol, amyl alcohol, butanol and isopentyl alcohol, the aforementioned acetone, as well as ethyl acetate, methyl tetrahydrofuran and tetrahydrofuran. Acetone is generally preferred, as in addition to acetone's effectiveness as a desorption solvent, acetone is very low-boiling and readily quantitatively removed by distillation or evaporation.

Suitable solvents for solvent extraction include methyl ethyl ketone and especially ethyl acetate, due to the latter's great affinity for HMF and levulinic acid, low boiling point (77 deg. C.) and ease of separation from water. As demonstrated in certain of the examples in the WO'136 application, virtually complete recovery of the sugars and of the HMF from mixture 18 was accomplished in WO'136 through a series of ethyl acetate extractions. Additionally, while the residual sugars recovered by other means were still suitable for being directly processed to ethanol in the subsequent ethanol fermentation step 26, those recovered following the quantitative extraction with ethyl acetate were observed to be significantly less inhibitory even under non-optimal conditions. A variety of other solvents have been suggested or used in the literature related to HMF and HMF derivative synthesis and recovery in biphasic systems, and these may be appropriate for use. Examples of other useful solvents are butanol, isoamyl alcohol, methyl ethyl ketone, methyl isobutyl ketone, diethyl ether, cyclopentyl dimethyl ether, methyl tetrahydrofuran, and methyl butyl ether.

Ethanol fermentation step 26 where employed can encompass any known process whereby a hexose sugars feed of the type represented by fermentation-ready sugars stream or portion 24 may be converted to one or more products inclusive of ethanol, at least in some part by fermentation means. Both aerobic and anaerobic processes are thus contemplated, using any of the variety of yeasts (e.g., *kluyveromyces lactis, kluyveromyces lipolytica, saccharomyces cerevisiae, s. uvarum, s. monacensis, s. pastorianus, s. bayanus, s. ellipsoidues, candida shehata, c. meliobiosica, c. intermedia*) or any of the variety of bacteria (e.g., *clostridium sporogenes, c. indolis, c. sphenoides, c. sordelli, candida bracarensis, candida dubliniensis, zymomonas mobilis, z. pomaceas*) that have ethanol-producing capability from the fermentation-ready sugars stream or portion 24 under aerobic or anaerobic conditions and other appropriate conditions. The particular yeasts (or bacteria) used and other particulars of the fermentations employing these various yeasts (or bacteria) are a matter for routine selection by those skilled in the fermentation art, though the examples below demonstrate the functionality of one common anaerobic yeast strain, *saccharomyces cerevisiae*. Given that the sugars stream or portion 24 derives from a process for making the acid dehydration product HMF, a yeast or bacteria that has been demonstrated for use particularly with sugars derived from a lignocellulosic biomass through acid-hydrolyzing the biomass and/or a cellulosic fraction from biomass may be preferred. For example, the aerobic bacterium *corynebacterium glutamicum* R was evaluated in Sakai et al., "Effect of Lignocellulose-Derived Inhibitors on Growth of and Ethanol Production by Growth-Arrested *Corynebacterium glutamicum* R", Applied and Environmental Biology, vol. 73, no. 7, pp 2349-2353 (April 2007), as an alternative to detoxification measures against organic acids, furans and phenols byproducts from the dilute acid pretreatment of biomass, and found promising.

Where present, the fermentation-ready sugars stream or portion 24 can, in whole or in part, also be used for other purposes beyond the production of ethanol. For example, sugars in stream or portion 24 can be recycled to the beginning of the acid dehydration step 16 for producing additional HMF. The hexose sugars represented by stream or portion 24 can also be hydrogenated to sugar alcohols for producing other biobased fuels and fuel additives (other than or in addition to ethanol), see, for example, U.S. Pat. No. 7,678,950 to Yao et al. The sugars in stream or portion 24 can be fermented to produce lysine or lactic acid according to known methods, or used for making another dehydration product such as levulinic acid. Still other uses will be evident to those skilled in the art, given the character of the sugars stream or portion 24 provided by the described process.

As mentioned previously, the acid dehydration step 16 is preferably conducted in a manner to limit the exposure of the HMF that is formed to acidic, elevated temperature conditions that lead to the formation of humins and other like degradation-type materials. Rapid heating of the hexose sugar solution 14 is consequently desirable. Further, once the aqueous hexose solution 14 has reached the desired reaction temperature range, the extent to which the aqueous hexose solution remains subject to the acidic, elevated temperature conditions is preferably also limited as taught and exemplified in the WO'136 application.

As a general matter, of course, it would be preferable to process sugar solutions 14 having a greater loading of the hexose sugars rather than a lesser loading, though some trade-offs were observed in terms of overall sugars accountability and in other respects, and these would need to be considered in determining the optimum conditions to be observed for a given feedstock.

For the particular example of a 40 percent dry solids loading HFCS 42 feed providing up to a 20 percent final dry solids concentration, using a shorter reaction time and a temperature toward the higher end seemed preferable according to the WO'136 application, for example, 5 minutes at 200 degrees Celsius. For HFCS 90, given the same acid starting concentration, the reaction temperature can be in the range of from 185 degrees to 205 degrees Celsius, the dry solids loading of hexose sugars in the sugar solution 14 can be from 30 to 50 percent and provide an 8 to 15 percent final dry solids concentration, and a reaction time can be from 5 to 10 minutes.

As an illustration of the considerations involved in processing one feedstock versus another, for HFCS 90 in contrast to HFCS 42, a final dry solids concentration of 20 percent could not be processed with the same overall sugars accountability, and a lower final dry solids concentration was indicated as preferable. For a final dry solids concentration of 10 percent, a reaction temperature of 185 degrees Celsius and a reaction time of 10 minutes were observed to provide favorable results. Favored conditions for the recovered sugars in stream or portion 24, it should be noted, may differ from those contemplated for freshly-supplied sugars in sugar solution 14 where recycle is contemplated for making additional HMF product or levulinic acid.

In any event, the heating to the desired reaction temperature is preferably accomplished in not more than 15 minutes, preferably is accomplished in 11 minutes of less, more preferably in not more than 8 minutes and still more preferably is accomplished in not more than five minutes. As demonstrated by WO'136's examples, rapid feeding of a quantity of ambient hexose sugar solution to a hot aqueous acid matrix (in two minutes) gave consistent improvements in one or more of HMF selectivity, yield and overall sugar accountability compared to less rapid feeding, even given the same elapsed time between when the quantity of hexose sugar solution was fully introduced and when cooling was initiated. More particularly, in a batch reactor combining the sugar solution 14 and the acid catalyst in a hot reactor already close to or at the desired reaction temperature provided improved results as compared to where the sugar solution 14 and acid catalyst are added to a reactor and then heated gradually together to the desired reaction temperature.

In regard to continuous processes, one suitable means for rapidly heating the sugar solution 14 and the acid catalyst would be direct steam injection. A commercially-available, in-line direct steam injection device, the Hydro-Thermal Hydroheater™ from Hydro-Thermal Corporation, 400 Pilot Court, Waukesha, Wis., injects sonic velocity steam into a thin layer of a liquid (such as the sugar solution 14) flowing from an inlet pipe through a series of gaps. Steam flow is adjusted precisely through a variable area nozzle to an extent whereby outlet fluid temperatures are claimed to be controllable within 0.5 degrees Fahrenheit over a large liquid turndown ratio. Turbulent mixing takes place in a specifically designed combining tube, with an adjustable degree of shear responsive to adjustments of the steam flow and the liquid flow through (or pressure drop across) the series of gaps. Devices of this general character are described in, for example, U.S. Pat. Nos. 5,622,655; 5,842,497; 6,082,712; and 7,152,851.

In WO'136's examples using such a device, the highest HMF yield and sugar accountability from HFCS 42 syrup included a system of sulfuric acid (0.5% by wt of sugars), an initial dry solids concentration of 20% and rapid heating of the reaction mixture by direct steam injection by means of a Hydro-Thermal Hydroheater™ with a system back pressure of 1.48-1.52 MPa, gauge (215-220 psig), a steam pressure of 1.90 MPa, gauge (275 psig), a time of 5-6 minutes at the reaction temperatures provided by the direct steam injection and with rapid cooling of the product mixture before pressure relief. The reaction control set point was 200 degrees Celsius, and the maximum temperature achieved at the end of the resting tube was 166 degrees Celsius. HMF was obtained with these conditions in up to 20% molar yield with greater than 90% total sugar accountability. There was virtually no visible production of insoluble humins.

For HFCS 90 syrup processed in the same apparatus, the highest HMF yield and sugar accountability included a system of sulfuric acid (0.5% by wt of sugars), an initial dry solids concentration of 10%, and rapid heating of the reaction mixture by direct steam injection with a system back pressure of 1.03 MPa, gauge (150 psig), a steam pressure of 1.38 MPa, gauge (200 psig), a time of 11 minutes at the reaction temperatures provided by the direct steam injection and with rapid cooling of the product mixture before pressure relief. The reaction control set point was 185 degrees Celsius, and the maximum temperature achieved at the end of the resting tube was 179 degrees Celsius. HMF was obtained from HFCS 90 with these conditions up to 31% molar yield with greater than 95% total sugar accountability. There was again virtually no visible production of insoluble humins.

The WO'136 application prescribes rapid cooling of the mixture 18 as a preferred further measure to limit the exposure of the HMF product to elevated temperatures and acidic conditions, and describes various ways in which this rapid cooling could be accomplished prior to the use of adsorption, solvent extraction, or a combination of these in separation step 20 as previously described, to yield an HMF product stream or portion 22 and a fermentation-ready sugars stream or portion 24 which can optionally be supplied to an ethanol fermentation step 26 for producing an ethanol product 28. However, for purposes of the present invention, and more particularly, for purposes of an integrated process as schematically illustrated in FIG. 3, given preferred temperatures for the oxidation of the HMF it will likely be preferable (after the separation step 20) to simply convey the HMF product stream or portion 22 directly to the subsequent oxidation step for oxidizing HMF in the stream or portion 22 to provide FDCA.

While a preferred integrated process embodiment schematically depicted in FIG. 3 will be described presently, it will be instructive to consider first an oxidation process 30 according to the present invention in isolation, in which an aqueous feed 32 comprising one or more dehydration products inclusive at least of HMF in a concentration of at least about five percent by weight (which aqueous feed 32 may be obtained from a process as described in the WO'136 application, or as previously indicated, may be obtained from any of a number of other sources or by other means) is processed in the presence of an HMF oxidation catalyst according to the present invention to yield products inclusive of FDCA.

Figure 2:
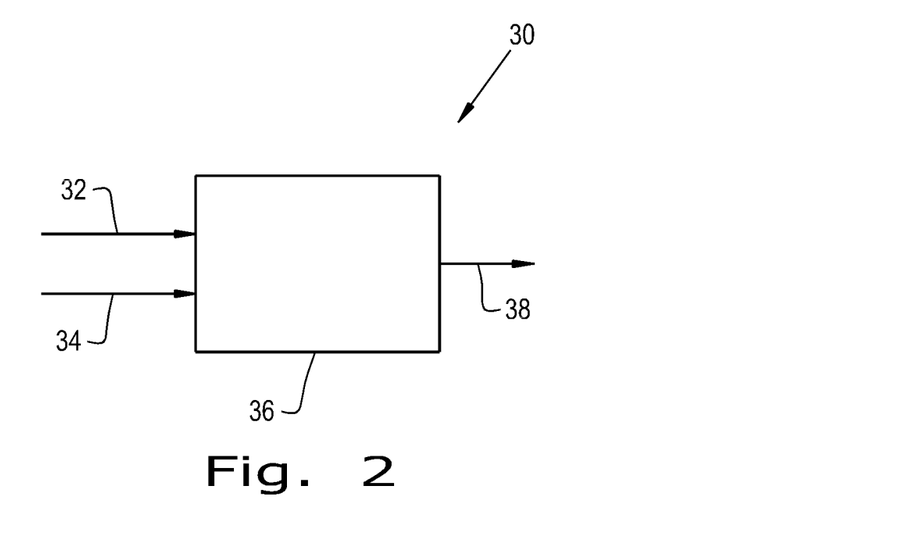
FIG. 2 schematically illustrates a process of the present invention according to a first aspect, for carrying out an oxidation of HMF in an aqueous feed comprised of one or more sugar dehydration products inclusive at least of HMF.

Accordingly, turning now to FIG. 2, the aqueous feed 32 undergoes oxidation by combination with an oxygen source 34 (which can be air, oxygen-enriched air, oxygen or a combination of oxygen with one or more other, inert gases) in a reactor 36, in the presence of a heterogeneous ruthenium-based catalyst, under conditions which are effective to carry out the oxidation. A product 38 comprising FDCA is thereby produced.

In one embodiment, the catalyst employs ruthenium as the sole active catalyst metal. In a further refinement, the catalyst is unsupported. In still a further refinement, the catalyst is an unsupported ruthenium oxide catalyst, and requires neither prior base treatment or a basic support to be fundamentally effective. The unsupported ruthenium oxide catalyst according to our studies does, however, demonstrate some differences in performance based on the pH of the incoming aqueous feed 32 at lower oxidation temperatures; at lower temperatures, a neutral pH favors FDCA production while higher temperatures were observed to be less sensitive to the pH of the incoming aqueous feed 32.

Suitable reaction temperatures in this regard range from about 70 degrees Celsius to about 170 degrees Celsius, preferably are in the range of from about 85 degrees Celsius to about 160 degrees Celsius, and more preferably are in the range of from about 90 degrees Celsius to about 150 degrees Celsius. At lower temperatures within the broader range of operable temperatures, as previously noted, the selectivity to certain oxidation products is to a degree dependent on the pH of the incoming aqueous feed; at basic values, selectivity to FDCA is reduced and production of maleic, succinic and fumaric acids increases. Within the more preferred range of operating temperatures, however, differences in the pH of the incoming aqueous feed had comparatively little effect on product distribution.

The catalyst loading can be from 0.5 to 30 percent by weight based on the weight of HMF in the aqueous feed, but preferably is used in the range of from 1 to 20 percent by weight based on the weight of HMF in the aqueous feed, and more preferably is employed at from 3 to 15 percent by weight based on the weight of HMF in the aqueous feed.

The HMF concentration in the aqueous feed is at least 5 percent by weight up to 30 percent by weight, preferably is from 5 percent by weight of the aqueous feed to 20 percent by weight of the feed, and more preferably is from 5 percent to 15 percent by weight of the aqueous feed.

The source of oxygen for performing the oxidation can be oxygen, oxygen-enriched air, air or another mixture of oxygen with one or more inert gases, for example, carbon dioxide. Preferably, the oxygen source is simply oxygen. From 0.5 MPa to 10 MPa (5 to 100 bar) of oxygen is present, though preferably oxygen is present at from 2.0 MPa to 9.0 MPa (20 to 90 bar) and more preferably is present at from 3.0 to 7.0 MPa (30 to 70 bar).

Batch reaction times or average residence times in a continuous reactor will be from 1 to 26 hours, preferably will be from 2 to 20 hours, and more preferably will be from 3 hours to 15 hours.

Reactor 36 can be configured in several ways to carry out the oxidation step. Because FDCA is sparingly soluble in water at ambient temperatures and because a heterogeneous solid ruthenium-based catalyst is employed, separation of the FDCA as it is formed from the solid heterogeneous catalyst is an important design consideration. In one embodiment, FDCA is hot-filtered away from the catalyst, by maintaining the temperature of the products above a temperature at which the FDCA remains water-soluble. This manner of operation would lend itself to a continuous fixed-bed, multitubular reactor design. Alternatively, the FDCA could be separated from the heterogeneous catalyst in a multi-vessel slurry process, by pumping a slurry of FDCA solids and of the ruthenium-based heterogeneous catalyst (e.g., unsupported ruthenium oxide) in water into a second vessel following the reactor 36 wherein the FDCA is dissolved in a solvent which substantially does not solubilize the catalyst, for example, methanol, then the FDCA/methanol solution is withdrawn from the vessel and the solid catalyst returned to the reactor 36. Evaporation of the methanol would then provide a high purity FDCA solid product. A number of industrially practiced examples of such multi-vessel slurry processes can be found. In another possible approach, a semi-batch stirred tank configuration can be considered wherein the catalyst is contained in baskets, as in a Carberry or Robinson-Mahoney type reactor, and the stirred tank taken offline for washing with methanol to remove FDCA solids deposited in the reactor and on the catalyst. Still another approach for dealing with the limited solubility of FDCA in water would involve forming an FDCA derivative in the reactor 36 that is substantially more soluble than FDCA, so that the FDCA derivative can be removed in solution from the reactor 36. The FDCA derivative, for example, the dimethyl ester of FDCA, may have beneficial applications of its own, or FDCA could be regenerated from the FDCA derivative by further processing according to known methods.

Figure 3:
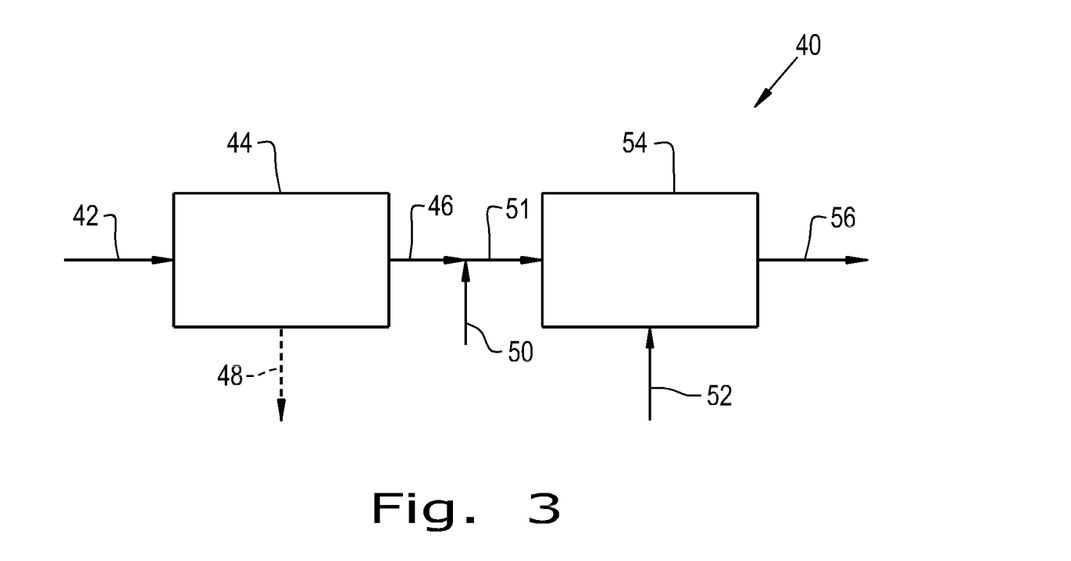
FIG. 3 shows an integrated process according to the second aspect of the present invention in a preferred embodiment, wherein a process according to the WO'136 application is used to produce an aqueous feed comprising one or more hexose dehydration products inclusive at least of HMF, and HMF in the aqueous feed is oxidized using a catalyst and process according to the instant application.

While the preparation of the aqueous feed 32 and the oxidation of HMF contained in aqueous feed 32 can take place independently of one another in time and/or place, in a preferred embodiment 40 illustrated schematically in FIG. 3, preferably the dehydration of hexose sugars in an aqueous solution to provide an aqueous feed containing HMF and the subsequent oxidation of the HMF in such feed are accomplished together in an integrated process. The preferred embodiment 40 has been summarized previously in relation to different modes of practicing a fast dehydration process of the type described in the WO'136 application, according to a second aspect of the present invention, but in general involves carrying out an acid-catalyzed dehydration of an aqueous hexose sugars solution 42 in a dehydration reactor 44. The dehydration of the hexose sugars in the solution 42 produces an aqueous HMF product 46 and optionally a residual sugars product 48 that may be obtained as a separate product from the aqueous HMF product 46, by carrying out a solvent extraction or adsorption/desorption step as described in relation to FIG. 1 (as step 20) to separate the residual sugars after the dehydration step from the HMF generated in the dehydration step.

Where the principal desired overall product(s) are the furanic oxidation products such as FDCA that are obtained by oxidizing HMF from the dehydration step, however, preferably the residual sugars product 48 will not be produced as a co-product, or if produced will be produced only for recycle back for joinder with the hexose sugars in solution 42, and with only so much of the residual sugars being produced in product 48 as necessary to avoid excessive deactivation of the ruthenium-based oxidation catalyst or other like difficulties in the subsequent oxidation step yet to be described.

Aqueous HMF product 46 is then conventionally diluted with the addition of water 50 to yield an aqueous HMF feed 51 to the oxidation step. In the oxidation step, the aqueous HMF feed 51 is combined with a source of oxygen 52 in a suitable oxidation reactor 54 in the presence of a ruthenium-based heterogeneous catalyst (not shown) and under suitable conditions for carrying out the oxidation, and furanic oxidation products including FDCA are produced in product 56. The oxidation reactor 54 and associated process can be as described in FIG. 2 above.

EXAMPLES

The present invention is further illustrated by means of the following, non-limiting examples:

Examples 1-9

A series of HMF oxidation reactions was performed at different temperatures with two sets of otherwise constant reaction conditions on a bench scale, using a Parr multireactor system (Parr Instrument Company, Moline, Ill.). For each run under a given set of conditions, a 75 mL reaction chamber was charged with a solution of HMF in water and ruthenium oxide and pressured with an oxygen source. The solution was heated to a desired temperature over a period of 20-30 minutes, accompanied by magnetic stirring at a controlled rate of 850 rpm. The reaction was continued for a time, then the solution was cooled and the heterogeneous mixture filtered to remove the solids. The oxidized products in the solids were isolated by washing the solids with methanol and then removing the methanol by rotary evaporation. HPLC analysis was performed on the filtrate and the solids after methanol washing. The catalyst was recovered and recycled.

For the series at different temperatures under a first set of conditions, HMF was oxidized at different reactor temperatures over a 3 hour reaction time with 10% dry solids, 10% ruthenium oxide catalyst by weight of HMF at 6.0 MPa (60 bar) of oxygen. The product compositions produced and the percentage molar yields of the various materials found in the product mixtures, whether oxidized products or unconverted HMF, were as shown in Table 1A. For the series under the second set of conditions, an additional four runs were conducted at various temperatures with 5% dry solids, 10% ruthenium oxide catalyst at 7.0 MPa (70 bar) of oxygen for a 6 hour reaction time. The results are shown for comparison in Table 1B, and demonstrate that the amount of HMF converted, product yields and overall accountability can be influenced by the reaction temperature employed.

TABLE 1A

| | | % Molar Yield | | | | |
|---|---|---|---|---|---|---|
| Example # | Temp C. | HMF | FDCA | FFCA | HMFCA | DFF |
| 1 | 100 | 13 | 2 | 27 | 1 | 47 |
| 2 | 120 | 0 | 24 | 55 | 0 | 9 |
| 3 | 130 | 1 | 66 | 28 | 0 | 0 |
| 4 | 140 | 1 | 64 | 10 | 0 | 0 |
| 5 | 160 | 0 | 26 | 0 | 0 | 0 |

TABLE 1B

| | | % Molar Yield | | | | |
|---|---|---|---|---|---|---|
| Example # | Temp C. | HMF | FDCA | FFCA | HMFCA | DFF |
| 6 | 85 | 19 | 3 | 31 | 1 | 46 |
| 7 | 100 | 3 | 10 | 53 | 0 | 34 |
| 8 | 120 | 0 | 36 | 49 | 0 | 3 |
| 9 | 130 | 0 | 69 | 1 | 0 | 1 |

Examples 10-14

A series of three experiments were conducted in parallel at three different dry solids concentrations in the reaction mixture, but otherwise identical conditions, namely, with a 3 hour reaction time at 120 degrees Celsius with 10% ruthenium oxide catalyst by weight of HMF and at 7.0 MPa (70 bar) of oxygen. An additional two experiments were conducted at two different dry solids concentrations at 160 degrees Celsius, but with otherwise identical conditions to those performed at 120 degrees Celsius. Analysis of the resultant product mixtures provided the results shown in Table 2, and demonstrates that the higher starting dry solid concentration produced more conversion of HMF and a greater overall amount of oxidized products than the lower starting dry solid concentrations.

TABLE 2

| Ex. # | HMF | FDCA | FFCA | HMFCA | DFF | Total knowns | Temp C. | Dry solids in reactor |
|---|---|---|---|---|---|---|---|---|
| 10 | 0 | 15 | 57 | 0 | 21 | 99 | 120 | 5 |
| 11 | 0 | 24 | 55 | 0 | 9 | 90 | 120 | 9 |
| 12 | 0 | 26 | 58 | 0 | 8 | 92 | 120 | 15 |

TABLE 2-continued

| Ex. # | HMF | FDCA | FFCA | HMFCA | DFF | Total knowns | Temp C. | Dry solids in reactor |
|---|---|---|---|---|---|---|---|---|
| 13 | 0 | 51 | 3 | 0 | 0 | 54 | 160 | 5 |
| 14 | 0 | 62 | 3 | 0 | 0 | 65 | 160 | 9 |

Examples 15-18

A series of four experiments were conducted at four different reaction times with 10% ruthenium oxide by weight of HMF at 100 degrees Celsius and 7.0 MPa (70 bar) air, at 6% dry solids. The runs were conducted at 1 hour, 3 hour, 6 hour, and 16 hour reaction times, with the results shown in Table 3. The reaction time significantly influences product composition and yield.

TABLE 3A

| Ex. # | Reaction time (hr) | % molar yield | | | | |
|---|---|---|---|---|---|---|
| | | HMF | FDCA | FFCA | HMFCA | DFF |
| 15 | 1 | 58 | 1 | 7 | 1 | 27 |
| 16 | 3 | 39 | 2 | 15 | 1 | 35 |
| 17 | 6 | 23 | 3 | 25 | 1 | 42 |
| 18 | 16 | 12 | 5 | 31 | 1 | 37 |

Examples 19-21

For comparison to Example 15, an additional experiment was conducted with the same reaction time of 1 hour and with the same other reaction conditions (6% dry solids, 10% ruthenium oxide by weight of HMF, 7.0 MPa (70 bar) air), except that the reaction temperature was 85 degrees Celsius rather than 100 degrees Celsius. Two further experiments were then conducted at the same 85 degree Celsius and 100 degree Celsius reaction temperatures and the same other reaction conditions, except that 7.0 MPa (70 bar) oxygen was used rather than 7.0 MPa (70 bar) air. These results are shown in Table 4.

TABLE 4

| Example # | Gas | Temp (deg. C.) | % Molar Yield | | | | |
|---|---|---|---|---|---|---|---|
| | | | HMF | FDCA | FFCA | HMFCA | DFF |
| 19 | Air | 85 | 21 | 4 | 29 | 1 | 43 |
| 20 | Oxygen | 85 | 1 | 19 | 72 | 0 | 25 |
| 21 | oxygen | 100 | 0 | 71 | 35 | 0 | 1 |

Examples 22-24

An aqueous HMF solution comprised of HMF (5% on a dry solids basis) was pressurized to 3.0 MPa (30 bar) with oxygen and heated to 100 degrees Celsius slowly over a period of 25 minutes. In one instance, no metal oxide was added to the aqueous HMF solution, while in the second instance, the same ruthenium oxide oxidation catalyst as used in previous examples was then added in the same proportion (at 10% by weight of HMF), and in the third instance, the ruthenium oxide was joined by zirconium acetate at 1% by weight of the HMF. After 3 hours at 100 degrees Celsius, the product mixtures from the three runs (no catalyst, Ru oxide catalyst and Ru oxide with zirconium acetate) were rapidly cooled as in previous examples and analyzed by HPLC. The molar yields of various products are as shown in Table 5, in percents, where FDCA is 2,5-furandicarboxylic acid (or dehydromucic acid), FFCA is formylfurancarboxylic acid, HMFCA is hydroxymethylfurancarboxylic acid and DFF is diformylfuran:

TABLE 5

| Example # | Catalyst | Percentage molar yield | | | | |
|---|---|---|---|---|---|---|
| | | HMF | FDCA | FFCA | HMFCA | DFF |
| 22 | No catalyst | 85 | 0 | 0 | 0 | 2 |
| 23 | Ruthenium oxide | 20 | 2 | 21 | 1 | 34 |
| 25 | Ru oxide + zirconium acetate | 29 | 2 | 19 | 1 | 38 |

Examples 25-26

An aqueous solution of HMF (5% dry solids in water) was oxidized in the presence of 10% by wt of HMF of ruthenium oxide by heating to 100 degrees Celsius for 1 hour with 7.0 MPa (70 bar) oxygen. The product mixture (Ex. 25) was then recycled for a second oxidation cycle under the same conditions (Ex. 26). The results are shown in Table 6 below.

TABLE 6

| Example # | Percentage molar yield | | | | |
|---|---|---|---|---|---|
| | HMF | FDCA | FFCA | HMFCA | DFF |
| 25 | 49 | 2 | 16 | 0 | 34 |
| 26 | 10 | 5 | 32 | 0 | 40 |

Example 27 with Comparative Examples 1 and 2

As may be observed from Table 7, at 100 degrees Celsius, with 30 bar of a 1:1 mixture of carbon dioxide and oxygen and in the presence of 10% ruthenium oxide and an additional 1% of zirconium acetate as a co-catalyst, about 55% of the HMF in a 5% dry solids aqueous feed was converted, with the predominant products being FFCA and DFF. Similar effects were seen in processing a 5% dry solids solution of HMF in acetic acid. By doubling the catalyst loading in acetic acid and introducing oxygen rather than an equal mixture of carbon dioxide and oxygen, HMF conversion rose to 70 percent, and the DFF molar yield was nearly doubled.

TABLE 7

| Exam- | | | Percentage molar yield | | | | |
|---|---|---|---|---|---|---|---|
| ple # | Solvent | Gas | HMF | FDCA | FFCA | HMFCA | DFF |
| 27 | Water | CO2/O2 | 43 | 2 | 16 | 0 | 33 |
| Comp. Ex. 1 | Acetic Acid | CO2/O2 | 45 | 5 | 1 | 0 | 38 |
| Comp. Ex. 2 | Acetic Acid | O2 | 30 | 1 | 4 | 0 | 66 |

Example 28

An aggregate sample of the products obtained from the oxidation of 5% and 9% dry solids aqueous HMF feeds at 160 degrees Celsius and 7.0 MPa (70 bar) oxygen was subjected to esterification with the addition of methanol and of 0.06 M bismuth (III) triflate in methanol solution. The combination was heated to 120° C. for 3 hours. The combination was cooled and excess methanol removed. $^1$H NMR of the product sample indicated a 1:1:1 ratio of FDCA, furan-2,5-carboxylic acid methyl ester, and furan-2,5-dicarboxylic acid methyl ester.

The invention claimed is:

1. A process for converting hydroxymethylfurfural to furanic products inclusive of 2,5-furandicarboxylic acid, comprising:
    combining a quantity of hydroxymethylfurfural with water to provide an aqueous solution containing at least five percent by weight of hydroxymethylfurfural; and
    combining the aqueous solution with an oxygen source in the presence of a heterogeneous ruthenium-based catalyst at a neutral or acidic pH; and
    oxidizing the hydroxymethylfurfural to furanic oxidation products inclusive of 2,5-furandicarboxylic acid,
    wherein the oxidation step is conducted in the substantial absence of any solvent for either hydroxymethylfurfural or 2,5-furandicarboxylic acid other than water.

2. A process according to claim 1, wherein the catalyst utilizes ruthenium as its sole catalytically active component.

3. A process according to claim 2, wherein the catalyst is unsupported.

4. A process according to claim 3, wherein the catalyst in an unsupported ruthenium oxide catalyst.

5. A process according to claim 1, wherein the 2,5-furandicarboxylic acid is separated from the heterogeneous catalyst at a temperature at which substantially all of the 2,5-furandicarboxylic acid remains in solution.

6. A process according to claim 1 wherein the process is conducted in a first vessel, then 2,5-furandicarboxylic acid is transferred while in solution from the first vessel to a second vessel accompanied by at least some of the heterogeneous catalyst from the first vessel, the transferred 2,5-furandicarboxylic acid and catalyst from the first vessel are combined in the second vessel with a material that is an effective solvent for 2,5-furandicarboxylic acid in the second vessel but which substantially does not solubilize the catalyst therein, then the catalyst is separated from the 2,5-furandicarboxylic acid, water and added solvent.

7. A process for making 2,5-furandicarboxylic acid from an aqueous solution comprised of one or more hexose sugars, comprising:
    subjecting the aqueous solution to a rapid acid-catalyzed dehydration to produce a product mixture including hydroxymethylfurfural, wherein the aqueous solution is heated from ambient temperature to a temperature greater than 175 degrees Celsius in the presence of an acid catalyst in less than 15 minutes;
    as necessary, adding water at an elevated temperature to the product mixture from the rapid acid-catalyzed dehydration to achieve an aqueous oxidation feed containing from 5 to 30 percent by weight of hydroxymethylfurfural in water; and
    combining the aqueous oxidation feed with an oxygen source in the presence of a heterogeneous ruthenium-based catalyst at a neutral or acidic pH; and
    oxidizing the hydroxymethylfurfural to furanic oxidation products inclusive of 2,5-furandicarboxylic acid,
    wherein the oxidation is carried out in the substantial absence of any solvent for either hydroxymethylfurfural or 2,5-furandicarboxylic acid other than water.

8. A process according to claim 7, wherein the product mixture from the rapid acid-catalyzed dehydration contains some residual sugars, and wherein residual sugars are separated from the product mixture before the oxidation of hydroxymethylfurfural in the product mixture to provide furanic oxidation products inclusive of 2,5-furandicarboxylic acid.

* * * * *